United States Patent [19]
Gandrud

[11] 3,988,134
[45] *Oct. 26, 1976

[54] DENTAL OFFICE SYSTEM

[76] Inventor: Stanton D. Gandrud, 20681 McClelland Road, Cupertino, Calif. 95014

[*] Notice: The portion of the term of this patent subsequent to Nov. 12, 1991, has been disclaimed.

[22] Filed: Nov. 6, 1974

[21] Appl. No.: 521,356

Related U.S. Application Data

[63] Continuation of Ser. No. 436,943, Jan. 28, 1974, Pat. No. 3,847,573, which is a continuation-in-part of Ser. No. 122,954, March 10, 1971, abandoned.

[52] U.S. Cl. .................. 55/319; 32/22; 32/33; 55/385 R; 55/419; 55/467; 55/429; 55/439; 55/446; 137/550; 251/324; 251/368
[51] Int. Cl.² .................................. B01D 45/08
[58] Field of Search ............ 55/220, 319, 385, 419, 55/418, 420, 468, 429, 520, 439, 446, 467; 32/22, 33, DIG. 1, DIG. 3; 137/544; 251/324, 368

[56] References Cited
UNITED STATES PATENTS

| | | | |
|---|---|---|---|
| 2,693,030 | 11/1954 | Gleason, Jr. et al. | 32/33 |
| 2,784,717 | 3/1957 | Thompson | 32/33 UX |
| 2,821,021 | 1/1958 | Winter | 32/33 |
| 3,017,886 | 1/1962 | Thompson | 55/385 UX |
| 3,051,175 | 8/1962 | Nugent | 32/33 UX |
| 3,078,579 | 2/1963 | Jones et al. | 32/33 |
| 3,305,927 | 2/1967 | Mitchell | 32/33 |
| 3,452,751 | 7/1969 | Austin, Jr. | 55/385 UX |
| 3,457,645 | 7/1969 | Swanson | 55/385 UX |
| 3,482,313 | 12/1969 | Stram | 32/33 |
| 3,484,941 | 12/1969 | Svard | 32/33 |
| 3,485,246 | 12/1969 | Austin, Jr. | 55/385 UX |
| 3,494,366 | 2/1970 | Starbuck et al. | 55/520 X |
| 3,612,089 | 10/1971 | Beguiristain | 32/33 X |
| 3,665,682 | 5/1972 | Ciavattoni et al. | 55/385 X |
| 3,847,573 | 11/1974 | Gandrud | 55/385 X |

Primary Examiner—Frank W. Lutter
Assistant Examiner—Kathleen J. Prunner
Attorney, Agent, or Firm—Limbach, Limbach & Sutton

[57] ABSTRACT

A dental office system including apparatus particularly adapted to high speed dental equipment. An aspirator operating valve having a coil spring trap catches inlays and crowns and other large pieces while permitting amalgum and other small pieces to pass without clogging the trap. A vacuum/venturi line avoids sludge buildup by constantly moving air through the lines. A water separator using a baffle arrangement avoids water creeping up the separator walls to reach and damage the vacuum pump. A slidable instrument console panel for ease of use by a dentist or his assistant includes automatic switches that operate when a dental handpiece is lifted.

15 Claims, 10 Drawing Figures

U.S. Patent  Oct. 26, 1976  Sheet 1 of 3  3,988,134
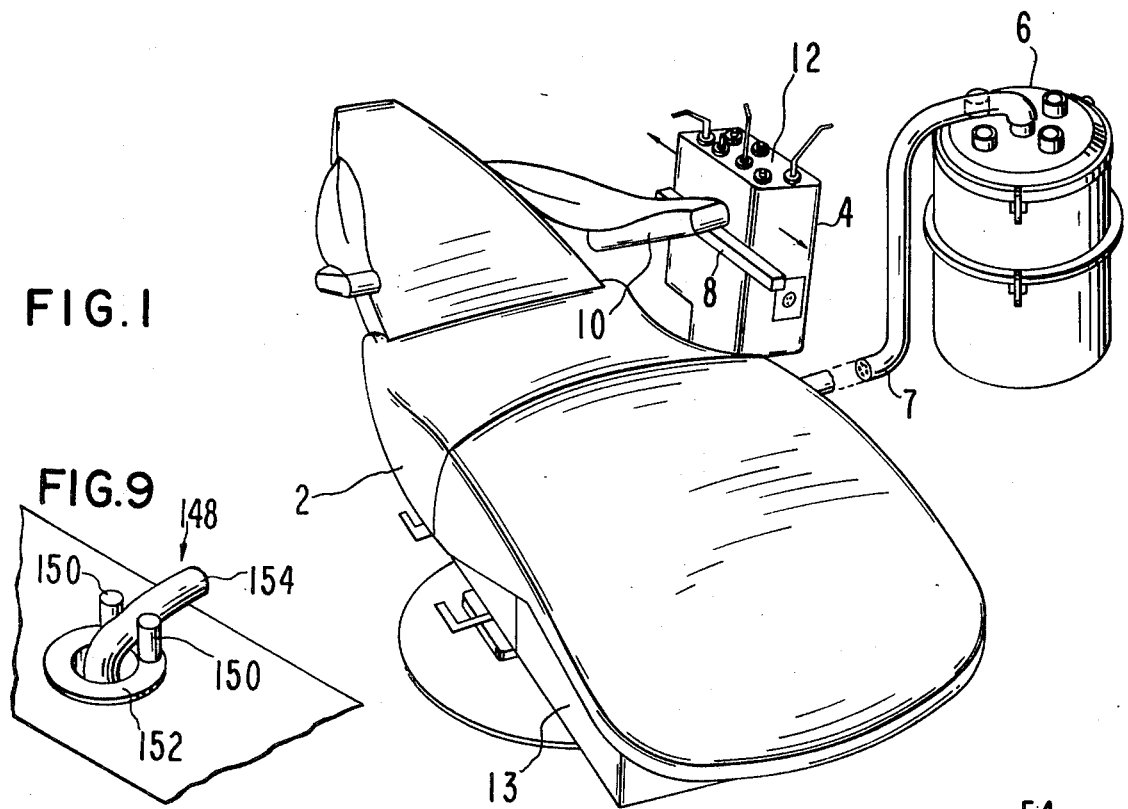
FIG. 1
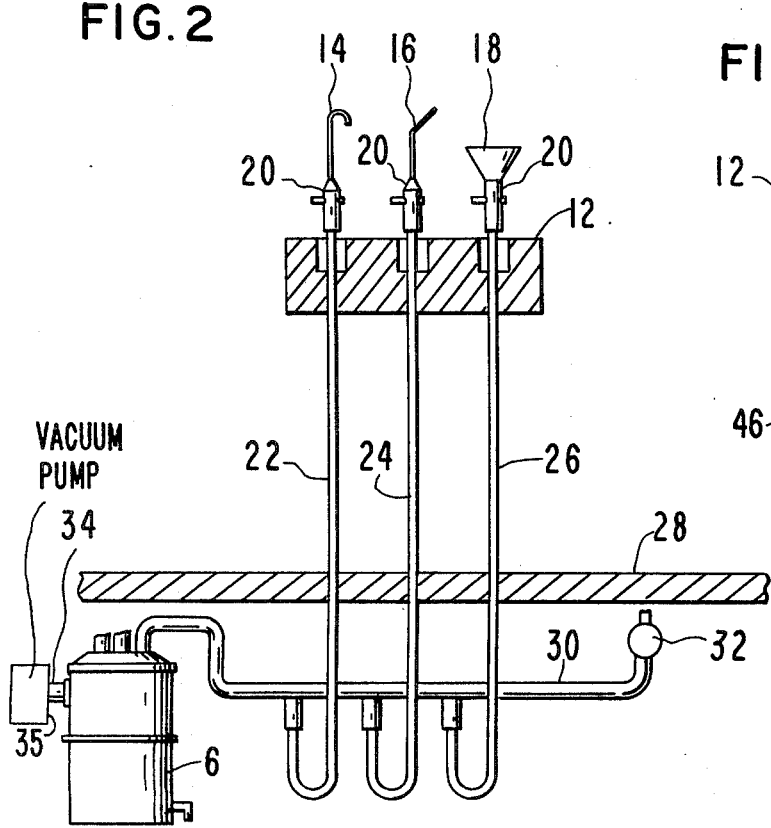
FIG. 9
FIG. 2
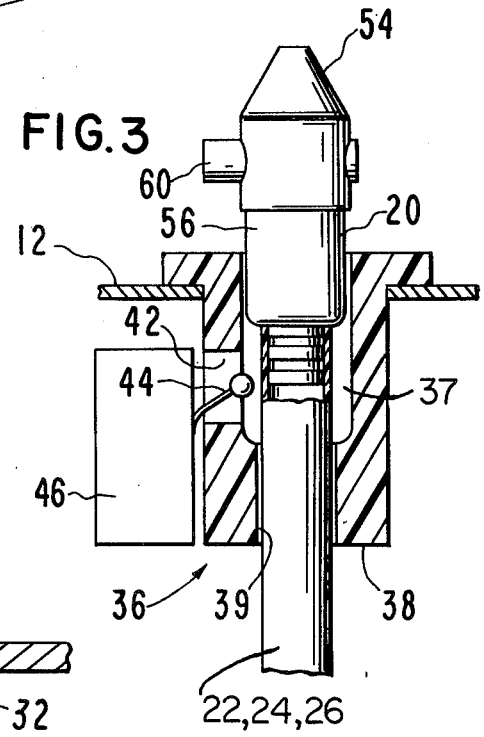
FIG. 3

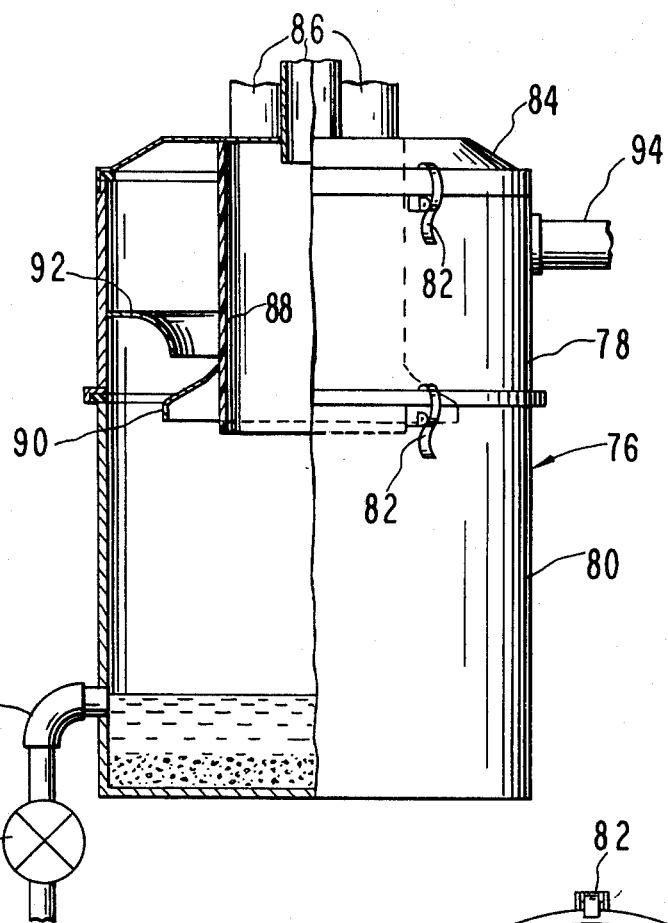
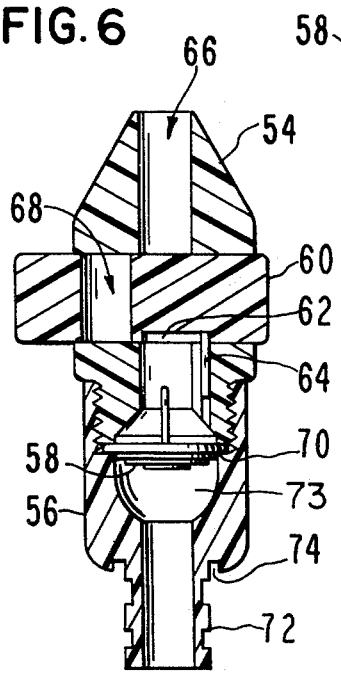
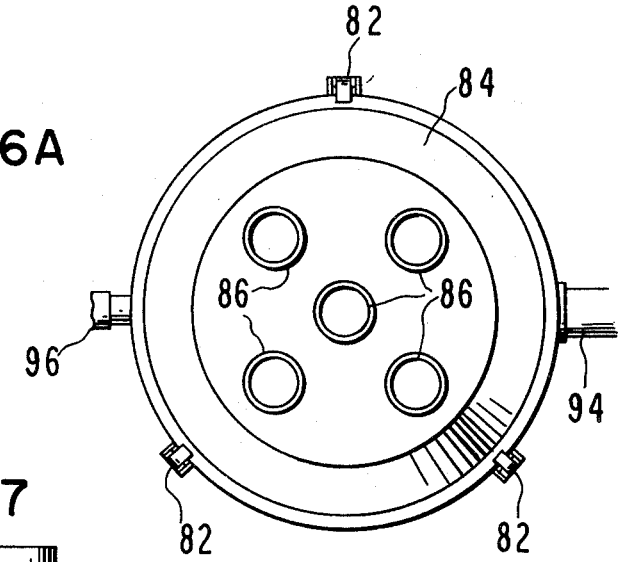
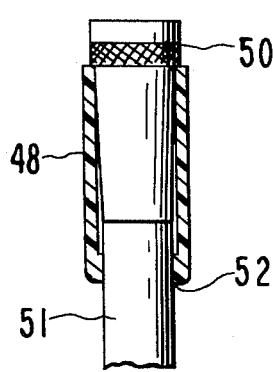

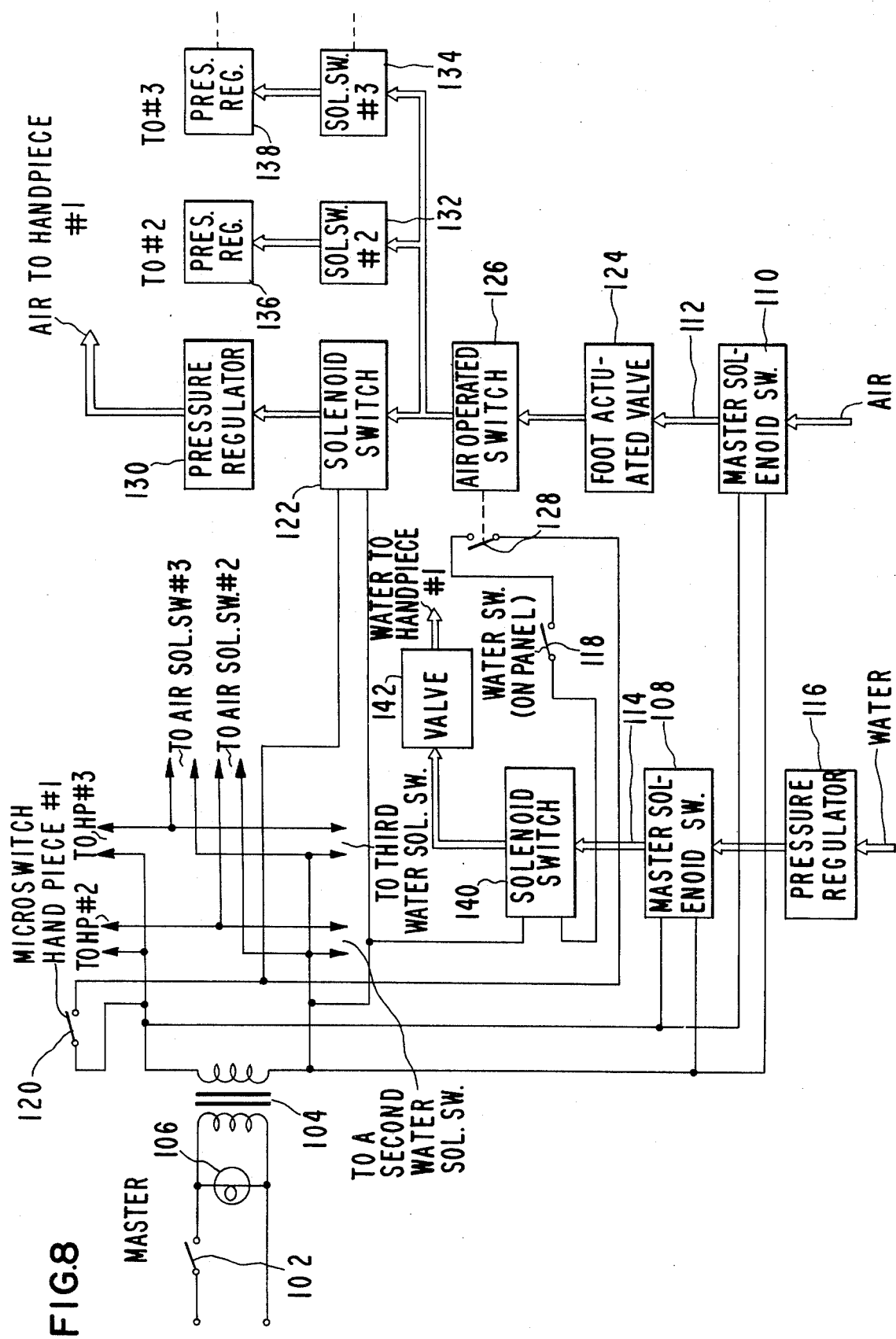

DENTAL OFFICE SYSTEM

This is a continuation of Ser. No. 436,943, filed Jan. 28, 1974 and now U.S. Pat. No. 3,847,573, which is, in turn, a continuation-in-part of application Ser. No. 122,954, filed Mar. 10, 1971, now abandoned.

BACKGROUND OF THE INVENTION

Substantial changes in dental office apparatus have occurred in recent years. For example, high speed equipment is replacing old conventional low speed drills. Even the design of the dental chair has changed to permit the dentist to work on a prone patient without the use of mirrors.

The changeover to high speed drilling equipment has resulted in the use of high speed vacuum systems to handle the large quantities of cooling water and solids encountered. Prior art vacuum systems have frequently encountered problems due to inadequate water separation in the line to the vacuum pump causing excessive wear and corrosion to the pump bearings and other components. Typically, even small amounts of moisture will result in a burnt out or frozen up pump in just a few weeks or months of operation.

A further problem in high vacuum systems has been the filling up of the lines with sludge and amalgam often requiring the lines to be cut, drained and replaced at a large cost and inconvenience.

The use of high vacuum systems presents a further problem in the increased tendency to pick up inlays, crowns, etc., from the mouth. Unless caught by some means near the dental handpiece, the object must be searched for in the precious metal collector of the water separator tank at great inconvenience. A countervailing requirement is that the means for catching such objects should not clog up the vacuum line by catching amalgum and other small pieces of material.

In order to permit both an unassisted dentist to reach the dental handpieces in the instrument console panel and for an assistant to also reach the same, when a dental chair of the new style is used, the panel is typically located in a compromise location. A means for locating the console within easy reach of the dentist or an assistant is desirable.

A further drawback in prior art dental handpieces/-panel configurations is the requirement that the dentist manually operate a switch in addition to picking up a handpiece.

SUMMARY OF THE INVENTION

The dental office system according to the present invention solves many of the above mentioned problems relating to modern high speed dental equipment. An improved water separator is provided to keep even small amounts of moisture from reaching the vacuum pump. A dual internal baffle arrangement causes a reverse eddy current and dead air space to counteract the tendency of water to creep up the sides of the separator.

In order to avoid filling the vacuum lines with sludge a vacuum/venturi system is provided wherein an automatic valve located at the end of each main vacuum line allows air to continually move through the vacuum lines thereby avoiding sludge buildup.

Means to catch inlays, crowns, etc., picked up by the high vacuum aspirator valve is provided by an improved valve having a coil spring. The spring catches large pieces accidentally picked up, yet it does not plug up with amalgum and other fine material that typically plugs up mesh screens.

The dental instrument console is improved by slidably mounting it for easy access by either the dentist working alone or by his assistant. In order to further simplify the instrument console and increase its efficiency, an automatic switch assembly associated with each handpiece removes the necessity to manually actuate a switch when a particular handpiece is to be used. In association with a high vacuum handpiece an automatic switch may be used to turn on the vacuum pump (if it is not left continuously running) or in association with an air or air/water handpiece the automatic switch permits actuation of the handpiece picked up when the dentist's foot pedal is depressed.

BRIEF DESCRIPTION OF THE DRAWINGS

FIG. 1 is a schematic perspective presentation of a portion of the dental office system according to the present invention, showing particularly the sliding instrument console, instrument controls in sliding drawer under the chair and a remotely located water separator.

FIG. 2 is a schematic diagram showing the water separator and vacuum/venturi line in conjunction with several vacuum dental handpieces.

FIG. 3 is a partially cut-away side elevation view of the automatic switch assembly shown in conjunction with the high vacuum valve and trap assembly.

FIG. 4 is a partially cut-away side elevation view of the water separator.

FIG. 5 is a plan view of the water separator of FIG. 4.

FIG. 6 is a cut-away side elevation view of the high vacuum valve and trap assembly of FIG. 3.

FIG. 6A is a plan view of the coil spring trap of the high vacuum valve and trap assembly of FIG. 6.

FIG. 7 is a partially cut-away side elevation view of an adaptor fitted over a conventional dental handpiece hose fitting.

FIG. 8 is a schematic diagram showing a typical dental handpiece control circuit for air operated drills.

FIG. 9 is a perspective view of a dental handpiece hose gripping assembly.

DESCRIPTION OF THE PREFERRED EMBODIMENTS

FIG. 1 shows a schematic perspective view of the dental office system according to the present invention. A conventional dental chair 2 is shown in conjunction with a sliding instrument console assembly 4 and an instrument control system in sliding drawer 13 and a remotely located water separator 6 connected via a hose 7. Instrument console assembly 4 is mounted on a slide bar 8 that is attached to the arm 10 or other rigid accessible portion of a dental chair. The slide bar mounting arrangement permits the instrument console assembly 4 to be moved to the forward part of the chair for ease of access when a dentist is working without an assistant. Conversely, the assembly 4 may be moved to the rear part of the chair when the dentist has an assistant. The specific details of the slide mechanism are not disclosed here since a number of means for providing a rigid yet horizontally slidable support are possible and are within the oridinary skill in the art. The sliding drawer 13 is mounted below the foot of chair 2 and contains air and water control components including pressure regulators for easy access by the dentist.

Instrument console assembly 4 has a panel 12 having a plurality of dental handpiece instruments. For example, as shown in FIG. 2, the panel may include a saliva ejector 14, a high volume expectorator 16, and a vacuum cuspidor 18. Each of the foregoing devices has a valve 20 that is shown in greater detail in FIGS. 3 and 6. A high vacuum is applied via lines 22, 24, and 26 to units 14, 16, and 18 respectively. Lines 22, 24, and 26 ordinarily pass through a floor loop 28, to form gas traps, and connect to a main vacuum line 30. Line 30 has an automatic vacuum adjusting valve 32 at one end thereof. Line 30 is connected at its opposite end to one of the inputs of water separator 6 that is shown in FIGS. 4 and 5 and described in greater detail in conjunction with those figures. Line 34 connects to a high vacuum pump 35 of conventional design. Separator 6 functions to remove water, blood and other liquids from the vacuum line to prevent moisture from damaging the vacuum pump. Also, small metal particles are caught in the previous metal collector in the base of separator 6.

The panel 12 of instrument console 4 also includes typically several air driven drills. High speed drills include the option of water cooling.

The location of automatic valve 32 permits the operation of a combination vacuum/venturi system. Valve 32 is adjusted to provide a continuous air flow in tube 30 while still maintaining a vacuum on tubes 22, 24 and 26 sufficient to move all materials encountered. It has been found that the lines are kept remarkably free of debris obviating the necessity to frequently shut down the system to clean out the lines. In a typical installation a plurality of lines may each serve several dentists or dental set ups. Each line, however, has an automatic valve at its remote end so that each line may be washed out without affecting the other lines. Thus a single separator tank and vacuum pump may serve as a central vacuum system.

FIG. 3 shows valve 20 in greater detail in conjunction with a switch assembly 36 located in panel 12. The lifting of a dental vacuum handpiece such as shown in FIG. 2 may complete an electrical circuit to actuate the vacuum pump. The lifting of a drill requiring air pressure or air and water permits control of the particular drill merely by the dentist's foot pedal as explained in conjunction with FIG. 8. The switch assembly includes a sleeve structure or grommet 38 having a cylindrical cutout portion 37 adapted to hold the base of valve 20 in a close relationship. A cylindrical hole 39 communicating with cylindrical cut out portion 37 is provided for vacuum lines 22, 24, 26 to pass through the bottom of sleeve 38. An aperture 42 is provided in the side of sleeve 38 to permit the actuating member 44 of a conventional microswitch 46 to extend into the central portion of the cylindrical opening of sleeve 38. The switch is closed when member 44 is extended; when valve 20, normally having a handpiece (not shown) attached thereto or a drill, is inserted into sleeve 38 the side of valve 20 moves microswitch member 44 toward the microswitch 46 to thereby open the switch. In order to permit the use of conventional handpieces or drills of different sizes than valve 20, with the switch assembly 36, an adapter must be used. FIG. 7 shows such an adapter 48 fitted over a conventional drill or handpiece air line hose fitting 50. The inside dimension will be machined to fit various makes of handpiece hose fittings and the outside dimensions are machined to fit the cylindrical cut out portion 37 (FIG. 3). A hole is defined by lip 52 at the bottom of the adapter for the air hose 51 to pass through. Adapter 48 is essentially a rigid tubular member having its open end sized to fit snugly over the fitting 50.

Referring now to the details of the valve 20 shown in FIGS. 3, 6 and 6A, the valve is basically formed of four pieces: a housing comprised of an upper member 54 and lower member 56 that screw together, a helically wound spring trap 58 and a sliding plunger actuator 60. Upper member 54 is a cylindrical body with a frustoconical top portion having a circular cross-sectional hole 66 bored axially through its center. The lower portion of upper member 54 is threaded to engage the threads of lower member 56. Actuator 60 is a cylindrical plug that fits closely into a hole bored crosswise through member 54. A slot 62 along actuator 60 engages a pin 64 mounted in member 54 to set limits on the sliding of actuator 60. In the closed position as shown in FIG. 6 the hole 66 is closed off completely. A throughput hole 68 in actuator 60 matches hole 66 when the actuator is in the right-hand position. The throughput hole is enclosed at all times by the valve housing. Some plunger type valves permit the throughput to show allowing blood to be seen by the patient. The valve is designed to accommodate the large quantities of cooling water used, for example, with high speed air turbine dental drills. The central aperture hole 66 is thus chosen to be of sufficient diameter to handle the volume flows to be encountered and to permit aspirator dental handpiece tubes 14, 16 (See FIG. 2) to be inserted therein. Flow path is essentially unimpeded due to the design of spring trap 58, when actuator 60 is in its right-hand position (as seen in FIG. 6); the diameter of the path is not decreased by the actuator when open.

The design of spring trap 58 in a helical form permits the effective catching of valuable crowns, inlays and fillings that heretofore have been picked up and lost in a high vacuum system. The trap does not impede the flow of the vacuum or the effluents through the valve. Quick recovery is made by simply unscrewing the upper and lower members. Small pieces of amalgam that tend to plug up screens pass through the coil spring and are captured in the separator tank.

The lower member 56 has a lip 70 to hold the edge of spring 58 against the lower edge of upper member 54. An enlarged chamber above spring 58 in member 54 is provided to allow room for particles caught by the spring 58 while not impeding vacuum and effluent flow by narrowing aperture 66. The chamber 73 below spring 58 tapers down to the original size of aperture 66. The extreme lower portion of member 56 is a ribbed cylinder 72 intended for gripping hose 40 to keep it from sliding off (See FIG. 3). The lower portion of the member 56 is undercut at 74 for the hose 40.

In a working embodiment of the valve 20, it has been found that Teflon is a desirable material for actuator 60 due to its continual natural lubrication and its free action under warm or cold conditions due to its superior expansion qualities. Members 54 and 56 are formed of Delrin, a durable, easy to clean, lightweight plastic. A tight leak-free fit is achieved.

Referring now to FIGS. 4 and 5, the water separator 6 is shown in greater detail. A cylindrical tank 76 is provided having a removable top portion 78 and a base portion 80 fastened together by conventional hand snaps 82 spaced around the unit. A removable lid portion 84 is also held on by snaps 82. A plurality of input pipes 86 are provided so that the separator may be used with several dental office setups. The separator is capable of handling up to about five independent input lines each having an automatic control valve at its remote end so that each provides continuous air movement. For example, FIG. 2 shows only one such line 30 connected to the separator.

Lines 86 open into cylinder 88 inside the separator and lines 86 and cylinder 88 fasten to lid member 84. The walls of cylinder 88 are solid and the bottom is open. The area of cylinder 88 should be at least four times the area of the inlet tubes 86 in order to cause the incoming air velocity to decrease to allow the water vapor to condense and drip to the bottom of the separator tank. An awning-like baffle 90 encircles the lower portion of cylinder 88. The bottom edge of cylinder 88 extends below the lower lip of baffle 90. A ring-shaped baffle 92 is mounted around the inside of the upper tank portion 78 above baffle 90. Baffle 92 extends outward from the interior wall and then curves downward somewhat like a portion of a doughnut surface. It has been found that in a tank subjected to negative pressures that water has a tendency to creep up vertical surfaces due to reduced surface tension. In the absence of baffles 90 and 92 water would reach the outlet pipe 94 in the side of the top portion 78 of the tank. Pipe 94 is connected to the vacuum pump (not shown) which would draw the water in and eventually causing damage to the pump. Instead of the water reaching outlet pipe 94, a "dead" air pocket is created at the base of the baffles. As the rush of air passes the baffles, some is diverted into the "dead air" space causing a reverse eddy current to reverse the upward flow of creeping water.

A waste outlet pipe 96 is provided in the side of the lower portion 76 of the tank. The pipe 96 is located somewhat above the tank bottom to permit valuable solids to collect; i.e., a precious metal collector. A check valve 98 permits the liquids to be expelled to a waste system. If desired, a float may be provided in the tank to sense a high water condition and shut off the pump motor.

FIG. 8 shows a typical control system for use with an instrument panel 12 (as in FIG. 1) having microswitch assembly actuators (as in FIG. 3). Basically, operation of a handpiece requires only that it be lifted from the panel, thus closing the microswitch contact, and that the foot pedal be stepped on. Typically, prior art systems required the lifting of the handpiece, the manual throwing of a toggle switch associated with the handpiece, and stepping on the foot pedal. The figure shows a control arrangement for three handpieces or drills, although any number could be used. The control system may be located in sliding drawer 13 below the dental chair 2 (see FIG. 1). When master switch 102 (on the panel 12) is closed power is applied to a voltage stepdown transformer 104 and an "on" lamp 106 lights. Solenoid switches 108 and 110 connected to the transformer secondary close and open the valves to provide an air supply at line 112 and a water supply at line 114. The water pressure is regulated by pressure regulator 116. The operator can choose either air alone or air and water at a handpiece; if switch 118 is closed, water will be available. If, for example, handpiece No. 1 is picked up, the microswitch 120 will close a circuit that will energize solenoid switch 122. If the foot pedal is depressed permitting air through pedal valve, the foot, air operated switch 126 closes contact 128 in response to the presence of the air pressure in the line and pressure regulator 130 regulates the air pressure to handpiece No. 1. In like manner, if handpiece No. 2 or No. 3 had been lifted the corresponding solenoid switch 132 or 134 and pressure regulator 136 to 138 would operate. If the water switch 118 had been closed solenoid switch 140 would also be actuated to supply water to regular valve 142 and the handpiece. A second and third water solenoid switch (as 140), valves (as 142), and water switches (as 118) are provided for the second and third handpieces.

FIG. 9 shows a perspective view of a dental handpiece hose gripping assembly 148 usable with either the vacuum handpieces or air/water drill previously described. A pair of cylindrical posts 150 are fixed to the flanged upper portion 152 of a sleeve or grommet 38 (as in FIG. 3). The posts' spacing is chosen somewhat smaller than the diameter of the hose 154 used with the handpiece. When a handpiece is lifted a tug on the hose results in gripping of the hose between the posts 150 thus eliminating elaborate spring arrangements encountered in some prior art dental set ups. To replace the handpiece the hose is lifted upward, freeing it from posts 150.

Obviously, numerous modifications and variations are possible in light of the above teachings. It is therefore to be understood that within the scope of the appended claims the invention may be practiced otherwise than as specifically described herein. For example, it will be apparent that the apparatus described have utility in environments other than a dental office.

I claim:

1. A dental office vacuum system comprising:
    water separator means having an input and an output for separating water from a line carrying air and water,
    a vacuum pump connected to said output downstream of said separator means,
    at least one main vacuum line connected at one end to said water separator means input,
    automatic valve means connected to the other end of said main line for providing continuous air flow through said main line when said vacuum pump is operating, and
    a plurality of dental handpieces connected through tubes to said at least one main vacuum line at a point between said automatic valve and said separator.

2. The combination of claim 1 wherein said dental handpieces each include a housing having an aperture therethrough and valve means therein for selectively blocking said aperture.

3. The combination of claim 2 wherein said aperture in the housing of the valve means of each of said dental handpieces is axial and said valve means further comprises a helical coil trap disposed in said axial aperture.

4. A system according to claim 3 wherein said valve housing is a substantially cylindrical housing and said aperture is through the axis thereof.

5. A system according to claim 4 wherein said valve means for selectively blocking said aperture comprises
    an aperture disposed crosswise through said housing substantially perpendicular to said axial aperture, and
    an actuator slidingly disposed in said crosswise aperture, said actuator having a throughput aperture aligning with said axial aperture when said actuator is in a first position and blocking said axial aperture when said actuator is in a second position.

6. A system according to claim 5 wherein said actuator throughput aperture remains within said valve housing throughout the movement of said actuator from said first position to said second position.

7. A system according to claim 6 wherein said valve housing comprises
   an upper member having a tapered end portion adapted for receiving an aspirator tube, said upper member including said crosswise aperture and actuator, and
   a lower member having a ribbed portion adapted to receive a hose, said members including means for removably engaging said members.

8. A system according to claim 7 wherein the periphery of said trap is held between said upper member and said lower member.

9. A system according to claim 8 wherein the axial aperture below said trap in said lower member has a larger diameter than the diameter of said axial aperture in said upper member.

10. A system according to claim 9 wherein said actuator has a guidance groove along a portion of its length and said valve housing further comprises a pin extending into said guidance groove for setting limits on the sliding of said actuator.

11. The combination of claim 1 further comprising automatic switch assembly means for removably holding each one of said dental handpieces, said assembly means comprising
   a recessed sleeve open at its top adapted to accept a dental handpiece, said sleeve having an aperture in its bottom for passing a hose therethrough and an aperture in the side wall thereof,
   switching means mounted adjacent said sleeve, said switching means having an extended actuating means passing through said aperture into the open portion of said sleeve, for placing said switching means in a first state in the presence of a dental handpiece in said sleeve, and for placing said switching means in a second state in the absence of a dental handpiece in said sleeve, and
   means responsive to said switching means in said second state for operating said vacuum pump.

12. The combination of claim 11 wherein said switching means comprises a microswitch.

13. The combination of claim 12 wherein said sleeve has a flanged upper portion for engaging a panel in which said sleeve may be mounted.

14. The combination of claim 13 further comprising adapter means having outside dimensions adapted to fit into said recessed sleeve and having inside dimensions adpated to accept a dental handpiece.

15. The combination of claim 13 further comprising means mounted on said automatic switch assembly for gripping a hose extending from said assembly, said means including a pair of upright members spaced apart a distance slightly less than the outside diameter of said hose.

* * * * *